United States Patent
Israelson et al.

(10) Patent No.: US 10,744,224 B2
(45) Date of Patent: Aug. 18, 2020

(54) ADHESIVE COMPOSITIONS

(71) Applicant: Coloplast A/S, Humlebaek (DK)

(72) Inventors: Dorrit Diana Israelson, Espergaerde (DK); Henrik Olsen, Copenhagen OE (DK); Charlotte Klein, Broenshoej (DK)

(73) Assignee: Coloplast A/S, Humlebaek (DK)

( * ) Notice: Subject to any disclaimer, the term of this patent is extended or adjusted under 35 U.S.C. 154(b) by 356 days.

(21) Appl. No.: 15/754,592

(22) PCT Filed: Aug. 24, 2016

(86) PCT No.: PCT/DK2016/050284
§ 371 (c)(1),
(2) Date: Feb. 23, 2018

(87) PCT Pub. No.: WO2017/032381
PCT Pub. Date: Mar. 2, 2017

(65) Prior Publication Data
US 2018/0243466 A1    Aug. 30, 2018

(30) Foreign Application Priority Data

Aug. 24, 2015 (DK) ................................ 2015 70544

(51) Int. Cl.
| | | |
|---|---|---|
| *A61L 24/04* | (2006.01) | |
| *A61L 24/06* | (2006.01) | |
| *C08L 33/02* | (2006.01) | |
| *C08L 23/08* | (2006.01) | |
| *C08L 1/00* | (2006.01) | |
| *A61K 47/00* | (2006.01) | |
| *C08L 53/02* | (2006.01) | |
| *A61L 24/00* | (2006.01) | |
| *A61L 27/06* | (2006.01) | |
| *A61L 24/08* | (2006.01) | |
| *A61L 24/10* | (2006.01) | |
| *C08L 23/14* | (2006.01) | |
| *C08L 23/20* | (2006.01) | |

(52) U.S. Cl.
CPC ......... *A61L 24/043* (2013.01); *A61L 24/0031* (2013.01); *A61L 24/046* (2013.01); *A61L 24/06* (2013.01); *A61L 24/08* (2013.01); *A61L 24/10* (2013.01); *A61L 27/06* (2013.01); *C08L 53/02* (2013.01); *A61L 2400/14* (2013.01); *C08L 23/08* (2013.01); *C08L 23/147* (2013.01); *C08L 23/20* (2013.01); *C08L 33/02* (2013.01)

(58) Field of Classification Search
None
See application file for complete search history.

(56) References Cited

U.S. PATENT DOCUMENTS

| | | | |
|---|---|---|---|
| 6,458,877 B1 | 10/2002 | Ahmed et al. | |
| 6,497,949 B1 | 12/2002 | Hyde et al. | |
| 9,422,463 B2 * | 8/2016 | Taylor | C09J 133/02 |
| 2002/0120032 A1 * | 8/2002 | Gothjaelpsen | A61F 5/443 |
| | | | 523/111 |
| 2004/0241246 A1 | 12/2004 | Lipman | |
| 2004/0243042 A1 | 12/2004 | Lipman | |
| 2006/0069370 A1 | 3/2006 | Ellingson et al. | |
| 2007/0079748 A1 | 4/2007 | Ahmed et al. | |
| 2008/0050554 A1 | 2/2008 | Toonen et al. | |
| 2008/0076860 A1 | 3/2008 | Ahmed et al. | |
| 2009/0171258 A1 | 7/2009 | Stroebeck et al. | |
| 2011/0251300 A1 | 10/2011 | Israelson | |
| 2013/0068386 A1 | 3/2013 | Lack et al. | |
| 2013/0122287 A1 | 5/2013 | Moeller et al. | |
| 2015/0045711 A1 | 2/2015 | Taylor et al. | |

FOREIGN PATENT DOCUMENTS

| | | |
|---|---|---|
| RU | 2393877 C2 | 7/2010 |
| WO | 9817212 A1 | 4/1998 |
| WO | 07092289 A2 | 8/2007 |
| WO | 07092290 A2 | 8/2007 |
| WO | 07092340 A2 | 8/2007 |
| WO | 07092350 A1 | 8/2007 |
| WO | 09155115 A2 | 12/2009 |
| WO | 2014159419 A1 | 10/2014 |

* cited by examiner

*Primary Examiner* — Tae H Yoon
(74) *Attorney, Agent, or Firm* — Coloplast Corp., Coloplast A/S; Nick Bauman

(57) ABSTRACT

Disclosed is an adhesive composition, devices including the adhesive composition and uses of the devices including the adhesive composition. The adhesive composition is for attachment to skin and includes an adhesive polymer component selected from a mixture of a polyethylene copolymer and polypropylene glycol (PPG), and styrene-ethylene/butylene-styrene (SEBS) block copolymer. The composition further includes polyolefin, polybutene, polyacrylic acid (PAA), and at least one further absorbent material.

14 Claims, No Drawings

ADHESIVE COMPOSITIONS

CROSS REFERENCE TO RELATED APPLICATIONS

This application is a 371 National Stage Application of International Application No. PCT/DK2016/050284, filed on Aug. 24, 2016, and which claims priority to Danish Patent Application No. PA 2015 70544, filed on Aug. 24, 2015. The contents of each are incorporated in their entirety by reference herein.

FIELD OF THE INVENTION

The invention relates to an adhesive composition for attachment to skin.

BACKGROUND

In connection with surgery for a number of diseases in the gastro-intestinal tract, in many cases, a consequence is that the colon, the ileum or the urethra has been exposed surgically. The patient is left with an abdominal stoma and the effluents or waste products of the body, which are conveyed through these organs, are discharged through the artificial orifice or opening and are collected in a collection bag. The bag is usually adhered to the skin by means of an adhesive wafer or plate having an inlet opening for accommodating the stoma. A separate ring-shaped adhesive and/or an adhesive paste may be used as an accessory for filling an area between the stoma and the adhesive wafer.

SUMMARY

Provided is an adhesive composition for attachment to skin, the composition comprising an adhesive polymer component selected from the group consisting of a mixture of a polyethylene copolymer and polypropylene glycol (PPG), and styrene-ethylene/butylene-styrene (SEBS) block copolymer; the composition further comprising polyolefin, polybutene, polyacrylic acid (PAA), and at least one further absorbent material.

In embodiments, the adhesive polymer component is a mixture of a polyethylene copolymer and polypropylene glycol (PPG).

In embodiments, the polyethylene copolymer is selected from the group consisting of poly(ethylene vinyl acetate) (PEVA), poly(ethylene vinyl acetate carbon monoxide), poly(ethylene butyl acetate), poly(ethylene vinyl alcohol), poly(ethylene butyl acrylate), and poly(ethylene butyl acrylate carbon monoxide).

In embodiments, the polyethylene copolymer is PEVA.

In embodiments, the adhesive polymer component is a styrene-ethylene/butylene-styrene (SEBS) block copolymer.

In embodiments, the composition comprises 10-15% (w/w), such as 10-13% (w/w), such as 10-12% (w/w) of the polyethylene copolymer. In embodiments, the composition does not comprise polyethylene copolymer.

In embodiments the polyethylene copolymer is a polar polyethylene copolymer. In embodiments, the polyethylene copolymer is poly(ethylene vinyl acetate) (PEVA). In embodiments the PEVA has a vinyl acetate content of at least 40% (w/w), such as at least 50% (w/w), such as at least 60% (w/w), such as at least 70% (w/w). In embodiments, the PEVA has a vinyl acetate content of 40-80% (w/w), such as 50-80% (w/w), such as 60-80% (w/w). In embodiments, the PEVA has a vinyl acetate content of 70% (w/w). In embodiments, the PEVA is LEVAMELT 700 from Lanxess.

In embodiments, the composition comprises 15-20% (w/w), such as 16-19% (w/w), such as 16-18% (w/w) PPG. In embodiments, the composition does not comprise PPG.

In embodiments, the PPG has an average molecular weight of 1.000-3.000 g/mol. In embodiments, the PPG has an average molecular weight of 2.000 g/mol. In embodiments, the PPG is Voranol 2000 L from Dow Chemical Company.

In embodiments, the composition comprises 4-9% (w/w), such as 5-8% (w/w), such as 6-7% (w/w) SEBS. In embodiments, the composition does not comprise SEBS.

In embodiments, the SEBS block copolymer has a polystyrene content of 20-40% (w/w) based on the final weight of the block copolymer, preferably 25-35% (w/w), more preferably 28-32% (w/w). In embodiments, the SEBS block copolymer is a Kraton G1726 M polymer from Kraton Performance Polymers Inc. having a polystyrene content in the range 29.2-31.6 (w/w).

In embodiments, the composition comprises 3-18% (w/w) polyolefin. In embodiments, the composition comprises 14-18% (w/w), such as 15-17% (w/w) polyolefin. In embodiments, the composition comprises 3-6% (w/w), such as 4-5% (w/w) polyolefin.

In embodiments, the polyolefin is a copolymer of propylene and ethylene. In embodiments, the polyolefin is Eastoflex E1016PL-1 Amorphous Polyolefin from Eastman Chemical Company.

In embodiments, the composition comprises 10-46% (w/w) polybutene. In embodiments, the composition comprises 11-15% (w/w), such as 12-14% (w/w) polybutene. In embodiments, the composition comprises 36-40% (w/w), such as 37-39% (w/w) polybutene.

In embodiments, the polybutene has a number average molecular weight of 4,000-8,000, such as 5,000-7,000, such as 6,000. In embodiments, the polybutene is Indopol Polybutene Grade H-18000 from INEOS.

In embodiments, the composition comprises 4-20% (w/w), such as 4-10% (w/w), such as 4-8% (w/w), such as 5-7% (w/w) PAA. In embodiments, the composition comprises 8-12% (w/w), such as 9-11% (w/w) PAA.

In embodiments, the PAA is crosslinked PAA. In embodiments, the PAA is partially neutralized PAA. In embodiments, the PAA is Carbopol 974P NF Polymer from Lubrizol Advanced Material, Inc. In embodiments, the PAA has a carboxylic acid content in the range 56-68%. In embodiments, the PAA has a viscosity of 20,000-50,000 cP, such as 25,000-45,000 cP, such as 25,000-40,000 cP, such as 29,400-39,400 cP at 25 degrees Celsius when measured with a Brookfield RVT at 20 RPM and neutralized to pH 7.3-7.8 using 0.5 wt % mucilage and spindle no. 6.

In embodiments, the composition comprises a total of 20-40% (w/w), such as 25-40% (w/w), such as 25-30% (w/w) or 29-35% (w/w) or 30-40% (w/w), such as 35-40% (w/w) of one or more further absorbent material(s).

In embodiments, the one or more further absorbent material(s) is selected from the group consisting of hydrocolloid, starch, water soluble salt, mono, di- and oligosaccharides, sugar alcohols, polypeptides, organic acids, inorganic acids, amino acids, amines, urea, super absorbent particles such as polyacrylic acid, glycols such as polyethylene glycol, fumed silica, and bentone.

In embodiments, the at least one further absorbent material is selected from the group consisting of hydrocolloid, starch, water soluble salt, mono, di- and oligosaccharides, sugar alcohols, polypeptides, organic acids, inorganic acids, amino acids, amines, urea, super absorbent particles such as polyacrylic acid, glycols such as polyethylene glycol, fumed silica, and bentone. In embodiments, the hydrocolloid is selected from guar gum, locust bean gum, pectin, potato starch, alginates, gelatine, xantan or gum karaya, cellulose derivatives, salts of carboxymethyl cellulose, sodium carboxymethyl cellulose, methyl cellulose, hydroxypropyl cellulose, hydroxyethyl cellulose, sodium starch glycolate, and polyvinylalcohol. In embodiments, the water soluble salt is selected from NaCl, $CaCl_2$, $K_2SO_4$, $NaHCO_3$, $Na_2CO_3$, KCl, NaBr, NaI, KI, $NH_4Cl$, $AlCl_3$, $CH_3COONa$, $CH_3COOK$, HCOONa, and HCOOK. In embodiments, the at least one further absorbent material is hydroxyethylcellulose with a weight average molecular weight in the range 500,000-2,000,000 g/mol, such as 750,000-1,500,000 g/mol, such as 800,000-1,200,000 g/mol, such as 1,000,000 g/mol. In embodiments, the at least one further absorbent material is Natrosol 250HX hydroethylcellulose from Ashland.

In embodiments, the composition further comprises a wax.

In embodiments, the composition comprises 1-5% (w/w), such as 2-4% (w/w) wax.

In embodiments, the wax is a microcrystalline wax. In embodiments, the wax is a polyethylene wax. In embodiments, the wax is Sasolwax 7837 from Sasol Wax GmbH.

In embodiments, the composition comprises 10-14% (w/w) polyethylene copolymer, 15-20% (w/w) PPG, 13-18% (w/w) polyolefin, 10-15% (w/w) polybutene, 1-5% (w/w) wax, 4-8% (w/w) PAA, and a total of 30-35% (w/w) of one or more further absorbent material(s).

In embodiments, the composition consists of 10-14% (w/w) polyethylene copolymer, 15-20% (w/w) PPG, 13-18% (w/w) polyolefin, 10-15% (w/w) polybutene, 1-5% (w/w) wax, 4-8% (w/w) PAA, and a total of 29-35% (w/w) of one or more further absorbent material(s).

In embodiments, the composition comprises 4-9% (w/w) SEBS, 3-6% (w/w) polyolefin, 35-41% (w/w) polybutene, 2-4% (w/w) wax, 8-12% (w/w) PAA, and a total of 35-40% (w/w) of one or more further absorbent material(s).

In embodiments, the composition consists of 4-9% (w/w) SEBS, 3-6% (w/w) polyolefin, 35-41% (w/w) polybutene, 2-4% (w/w) wax, 8-12% (w/w) PAA, and a total of 35-40% (w/w) of one or more further absorbent material(s).

In embodiments, the composition has an absorption at 2 hours, measured as described herein, of at least 0.1 $g/cm^2/2$ h, such as at least 0.15 $g/cm^2/2$ h, such as 0.15-3.0 $g/cm^2/2$ h. An absorption of at least 0.1 $g/cm^2/2$ h is deemed acceptable for ensuring that the composition can absorb sufficient liquid to properly transport moisture away from the skin surface and keep the skin dry. A higher absorption, such as at least 0.15 $g/cm^2/2$ h, is preferable, provided that such higher absorption does not lead to an insufficient gel strength.

In embodiments, the composition has an absorption at 24 hours, measured as described herein, of at least 0.5 $g/cm^2/24$ h, such as at least 0.6 $g/cm^2/24$ h, such as 0.6-1.1 $g/cm^2/24$ h. An absorption of at least 0.5 $g/cm^2/24$ h is deemed acceptable for ensuring that the composition can absorb sufficient liquid to properly transport moisture away from the skin surface and keep the skin dry. A higher absorption, such as at least 0.6 $g/cm^2/24$ h, is preferable, provided that such higher absorption does not lead to an insufficient gel strength.

In embodiments, the composition has a gel strength, measured as described herein, below 3 N, such as below 2 N, such as below 1 N. In embodiments, the composition has a gel strength, measured as described herein, in the range 0.75-1.5 N or 1-2 N. A gel strength of below 3 N is deemed acceptable for ensuring that residue is very rarely left on the skin when removing an adhesive composition that has absorbed liquid. Preferably, the gel strength is below 2 N, which ensures that practically no residue is left on the skin when the adhesive composition has absorbed liquid and is subsequently removed from the skin.

In embodiments, the composition has an absorption at 2 hours, measured as described herein, of 0.15-0.30 $g/cm^2/2$ h and an absorption at 24 hours, measured as described herein, of 0.6-1.1 $g/cm^2/24$ h, and a gel strength, measured as described herein, in the range 0.75-1.5 N. A composition with absorption and gel strength in these ranges exhibit a good balance between absorbent and cohesive properties.

Provided is an adhesive composition for attachment to the skin, the composition comprising an adhesive polymer and one or more absorbent materials, wherein the composition has an absorption at 2 hours, measured as described herein, of 0.15-0.30 $g/cm^2/2$ h and an absorption at 24 hours, measured as described herein, of 0.6-1.1 $g/cm^2/24$ h, and a gel strength, measured as described herein, in the range 0.75-1.5 N.

In embodiments, the composition comprises polyacrylic acid.

In embodiments, the composition has a $G^*$ at 1 Hz, measured as described herein, in the range 45,000-1,500,000 Pa. In embodiments, the $G^*$, measured as described herein, at 40 Hz is in the range 200,000-3,000,000 Pa. In embodiments, the $G^*$, measured as described herein, at 10 Hz is in the range 100,000-2,500,000 Pa. In embodiments, the $G^*$, measured as described herein, at 0.1 Hz is in the range 15,000-1,000,000 Pa. In embodiments, the $G^*$, measured as described herein, at 0.003 Hz is in the range 3,000-400,000 Pa. In embodiments, the composition has $G^*$ values within the above recited ranges for all mentioned frequencies. In preferred embodiments, the composition has a $G^*$ at 1 Hz, measured as described herein, in the range 75,000-1,000,000 Pa, such as 75,000-500,000 Pa, such as 75,000-300,000 Pa.

In embodiments, the composition has a tan(delta) at 1 Hz, measured as described herein, in the range 0.5-3. In embodiments, the composition has a tan(delta) at 40 Hz, measured as described herein, in the range 0.5-2. In embodiments, the composition has a tan(delta) at 10 Hz, measured as described herein, in the range 0.5-3. In embodiments, the composition has a tan(delta) at 0.1 Hz, measured as described herein, in the range 0.5-3. In embodiments, the composition has a tan(delta) at 0.003 Hz, measured as described herein, in the range 0.35-2.5. In embodiments, the composition has tan(delta) values within the above recited ranges for all mentioned frequencies. In preferred embodiments, the composition has a tan(delta) at 1 Hz, measured as described herein, in the range 0.6-1.5, such as 0.7-1.0 or 1.0-1.5.

$G^*$ and tan(delta) values in the above ranges for various frequencies ensure that the composition has a good balance between elastic and plastic properties.

In embodiments, the composition is mouldable. In embodiments, mouldable is defined as being capable of significant non-elastic deformation when a user applies pressure to the composition. In embodiments, the composition is capable of at least 10%, such as at least 20%, such as at least 30% non-elastic deformation. By non-elastic deformation is meant that the composition essentially retains its shape after deformation with elastically reverting to its original shape. In embodiments, the composition retains at least 70%, such as at least 80%, such as at least 90% of its adhesion at 10% deformation. In embodiments, the composition retains at least 70%, such as at least 80%, such as at least 90% of its adhesion at 20% deformation. In embodiments, the composition retains at least 70%, such as at least 80%, such as at least 90% of its adhesion at 30% deformation. In this context, adhesion is measured as peel force.

Provided is an adhesive device for attachment to a skin surface of a user, the device comprising an adhesive composition as described herein and at least one release liner.

In embodiments, the device has a skin-facing surface and a surface facing away from the skin during use, and the release liner is disposed on the skin-facing surface.

In embodiments, a second release liner is disposed on the surface facing away from the skin during use.

In embodiments, the adhesive device is ring or oval shaped with a through-going hole for fitting around a stoma of the user.

In embodiments, the outer diameter of the device is in the range 30-60 mm, such as 40-50 mm. If the device is not circular, the outer diameter is to be understood as the maximum diameter, meaning the maximum length from edge to edge of a line through the centre of the device.

In embodiments, the diameter of the hole is in the range 10-25 mm, such as 15-20 mm. If the hole is not circular, the outer diameter is to be understood as the maximum diameter, meaning the maximum length from edge to edge of a line through the centre of the hole. The device may be made in versions with different sized holes in order to fit around different sized stomas.

In embodiments, the thickness of the device, including release liner(s) is in the range 3.5-5.5 mm, such as 4-5 mm. In embodiments, the thickness of the device, excluding release liners, is in the range 2-3 mm.

In embodiments, the device is an adhesive barrier ring for fitting around a stoma.

Provided is a use of the adhesive device as described herein, comprising the steps of
providing the adhesive device,
removing one or more release liners from the device,
attaching the device to a skin surface surrounding a stoma.

In embodiments, the use comprises a further step of attaching the device to an adhesive baseplate of an ostomy device. In embodiments, the adhesive device is attached to the baseplate before the adhesive device is attached to the skin. In such a situation, the adhesive device is first adhered to the baseplate and the baseplate with the adhesive device is then attached to the skin surrounding the stoma. In embodiments, the adhesive device is attached to the skin and the baseplate is subsequently attached to the adhesive device and/or the skin surrounding the stoma.

DETAILED DESCRIPTION

Provided is an adhesive composition for attachment to skin. In embodiments, the adhesive composition is for attachment around the stoma of an ostomy device user. The adhesive composition may be used to provide a seal around the stoma and can be used in combination with a regular ostomy device comprising a collecting pouch and an adhesive wafer. In such a situation, the user will sometimes start by fitting the adhesive composition closely around the stoma and will then apply the adhesive wafer of the ostomy device on top of or immediately next to the adhesive composition. Alternatively, the user may start by applying the adhesive composition to the adhesive wafer of the ostomy device before attaching the combined device to the skin surrounding the stoma. In either way, a tight and secure seal can be provided around the stoma, thereby protecting against leakage.

The adhesive composition is absorbent, meaning that it is capable of absorbing liquid from the surroundings. This will allow the composition to absorb moisture from the skin around the stoma, which will help keep the skin surface dry, thereby preventing damage to the skin.

The adhesive composition is preferably mouldable, meaning that it can be shaped by the user applying pressure to the composition. By being mouldable, the composition can be shaped to closely match the shape of a given stoma and thereby provide a tight seal around the stoma.

In order to use the adhesive composition, any release liners are first removed and the adhesive compositions, typically in the form of a ring, is placed on the skin surrounding the stoma. The adhesive composition may then be moulded by pressing it in order to make it fit closely around the stoma. When the adhesive device has been secured around the stoma, a regular ostomy device, including an adhesive wafer and a collecting bag, may be attached to the skin and/or the outer surface of the adhesive device around the stoma.

After use, the composition is removed from the skin, optionally together with the ostomy device, and discarded.

When designing an adhesive composition for use on the skin, it is preferable that the composition can absorb moisture from the skin and that it can be easily removed in one piece. Generally, when an adhesive composition absorbs liquid, the adhesive composition will swell and become less cohesive. In other words, absorption of liquid will to some degree compromise the cohesiveness or structural integrity of the adhesive composition and will increase the risk that the adhesive breaks apart when removed from the skin. Such breaking apart during removal is referred to as cohesive failure and will result in adhesive residue being left on the skin of the user. This is problematic because such residue will be difficult to remove and will make it hard to attach a new adhesive to the skin.

For these reasons, it is desirable to achieve a good balance between absorption and cohesion. A high absorption will make sure the skin is kept dry and healthy while a high cohesion will mean that the adhesive can be removed in one piece without leaving significant residue.

The present inventors have identified adhesive compositions that strike a good balance between absorption and cohesion. Particularly, the inventors have found that adhesive compositions with ingredients within the claimed ranges will ensure both sufficient absorption and cohesion.

While the capabilities of absorption for the present adhesive composition are similar to traditional hydrocolloid adhesives, the new composition provides an additional high gel-strength, which makes the seal coherent and durable. Thus, during wear-time, the new composition will not dissolve and erode as easily because the increased gel-strength prevents it from breaking up into little pieces. In regards to pouch system change, this means that the new adhesive composition should leave less residue and come off in one piece along with the baseplate. Moreover, a high durability should increase the possibility of extended wear-time if needed.

Dynamic Mechanical Analysis (DMA)

The DMA was carried out as follows by a frequency sweep at 32° C. and 1% CD (controlled deformation). Samples were prepared by thermoforming to a 1 mm thick adhesive film between two release liners. With a punching tool, a round sample of 25 mm in diameter was cut out. The release liners were removed and the samples placed in an Anton Paar Physica MCR 301 rheometer. The geometry applied was parallel plates 25 mm and the force applied was 5 N. After applying 5 N force, 15 minutes of thermal equilibration of the samples at 32° C. were carried out before the measurements.

Moisture Absorption

Samples were prepared by thermoforming to a 1 mm thick adhesive film between two release liners. With a punching tool, samples were punched out. Sample size was 25×25 mm. The release liners were removed. The samples were glued to an object glass and placed in a beaker with physiological salt water and placed in an incubator at 37° C.

The sample was weighed at the outset (M(start)) and after 2 hours (M(2 hours) and/or 24 hours (M(2 hours)). Before weighing, the object glass was dried off with a cloth. For a 25×25 mm sample the area was 6.25 cm$^2$ (the surface edges were left out of the area). The moisture absorption may be calculated as: Water absorption after 2 hours=(M(2 hours)–M(start))/6.25 cm$^2$. The result is in the unit g/cm$^2$ per 2 hours. Water absorption after 24 hours=(M(24 hours)–M(start))/6.25 cm$^2$. The result is in the unit g/cm$^2$ per 24 hours.

Gel Strength

The cohesiveness or structural integrity of the adhesive composition following significant absorption is evaluated by testing the gel strength of the adhesive composition. A 1 mm thick sample of the adhesive composition is immersed in isotonic saline for 24 hours and the strength of the resulting swelled adhesive is tested by pressing a probe into the gel and measuring the distance travelled as a function of the force. A low number means that the probe is only able to be pushed a short distance into the sample at a given force, thus signifying a high gel strength, corresponding to a high cohesion and structural integrity.

EXAMPLES

The following materials were used in the tested compositions:

Cellulose: Natrosol 250HX hydroethylcellulose from Ashland.

Gelatine: UF 220 from PB Gelatins.

Guar Gum FG-200 from Nordisk Gelatine.

Poly(acrylic acid) (PAA): Carbopol 974P NF Polymer from Lubrizol Advanced Material, Inc.

Polybutene: Indopol Polybutene Grade H-18000 from INEOS.

Poly(ethylene vinylacetate) (PEVA): Levamelt 700 from Lanxess. Pre-irradiated to increase molecular weight, 22 kGy.

Polyolefin: Eastoflex E1016PL-1 Amorphous Polyolefin from Eastman Chemical Company.

Polypropylene glycol (PPG): Voranol 2000 L from Dow Chemical Company.

Potato starch M3 from Kartoffelmelcentralen in Denmark.

Sodium carboxy methyl cellulose (CMC): Akucell AF 2881 from Akzo.

Styrene-ethylene/butylene-styrene (SEBS) block copolymer: Kraton G1726 M polymer from Kraton Performance Polymers Inc.

Wax: Sasolwax 7837 from Sasol Wax GmbH.

The components were mixed on a Herman Linden Z blade mixer at a chamber temperature of 95° C. and a mixing speed of 20 rpm. The polymer components were added first and mixed. Then the absorbent components were added to the mixture and further mixed.

Measurements were carried out on four exemplary adhesive compositions falling within the scope of the invention (compositions number 56, 86, 61, and 94).

For comparison, measurements were also carried out on two commercial adhesive barrier ring products, namely the Eakin barrier ring from ConvaTec Inc. and the Adapt barrier ring from Hollister Inc. Analysis performed by the inventors has shown that the Eakin barrier ring is a polyolefin-based adhesive comprising hydrocolloids, most likely a type of cellulose and guar gum. Importantly, the Eakin barrier ring does not comprise poly(acrylic acid). The Adapt barrier ring also does not comprise poly(acrylic acid). These products were measured as described herein, also using a sample thickness of 1 mm.

The composition of the tested adhesives is indicated in the table below. The amount of the different components are all given as % (w/w). Absorption after 2 hours is given as "Abs, 2 h", is measured as described herein and has the unit g/cm$^2$/2 h. Similarly, absorption after 24 hours is indicated as "Abs, 24 h", is measured as described herein, and has the unit g/cm$^2$/24 h. Gel strength is measured as described herein and has the unit Newton (N).

| | Composition number/product | | | | | |
|---|---|---|---|---|---|---|
| | 56 | 86 | 61 | 94 | Eakin | Adapt |
| EVA | 11.2 | 12.52 | | | | |
| PPG | 16.8 | 18.78 | | | | |
| SEBS | | | 6.2 | 6.618 | | |
| Polyolefin | 13.7 | 16.5 | 3.1 | 3.3 | | |
| Polybutene | 11.6 | 14 | 37.2 | 39.78 | | |
| Wax | 2.6 | 3.1 | 3.1 | | | |
| PAA | 5 | 6 | 20 | 15 | | |
| Cellulose | 20 | 18 | 20 | 15 | | |
| Guar gum | | | 5 | 5 | | |
| CMC | | 4 | 5.3 | 10.3 | | |
| Gelatine | | 7.1 | | | | |
| Alginate | 19.1 | | | | | |
| Potato starch | | | | 5 | | |
| Abs, 2 h | 0.19 | 0.20 | 0.22 | 0.29 | 0.40 | 0.46 |
| Abs, 24 h | 0.67 | 0.62 | 0.81 | 1.04 | 0.84 | 1.13 |
| Gel strength | 1.1 | 1.2 | 0.9 | 0.9 | 4.6 | 5.1 |

All of the tested compositions, including the two comparative examples with the commercial Eakin and Adapt products, display sufficient water absorption at 2 h and 24 h to be usable on skin. The Eakin and Adapt products display somewhat higher absorption after 2 h than the tested inventive compositions. After 24 h, the absorption has levelled out, with the compositions 56 and 86 showing a tendency to be slightly lower than the rest, although still well within the range usable for skin adhesives.

The inventive compositions display significantly higher gel strength (lower numbers in the gel strength test as described herein) when compared to the commercial adhesive products. This means that the inventive compositions are much more cohesive after absorption and retain their structural integrity, even after having absorbed large amounts of liquid. In use, this means that the inventive compositions can easily be removed from the skin in one piece after use, without leaving significant residue on the skin of the user.

In conclusion, the inventive compositions all display a good balance between sufficient absorption and excellent gel strength. This means that the compositions are capable of absorbing moisture and keep the skin sufficiently dry during use, while at the same time maintaining their cohesion and structural integrity enough so that the adhesive composition does not fall apart during removal leaving residue on the skin.

It is hypothesized that the balance between the polymer adhesive ingredients and the absorbent materials in the composition gives rise to these beneficial properties. In particular, the inventors hypothesize that the use of PAA is an important factor in achieving the balance between good absorption and good cohesion. As is evident from the table above, the exact nature of the additional absorbent materials does not appear to be essential. Also, the presence of a wax is not essential.

Importantly, the beneficial effects are obtained with both a PEVA-PPG mixture and with a SEBS copolymer as the adhesive polymer component.

As illustrated by the Eakin and Adapt commercial products, it is possible in other ways to achieve any one of absorption, cohesion, and mouldability in isolation. The challenge faced by the instant inventors was to create an adhesive composition that was both sufficiently absorbent, and cohesive after absorption, as well as, preferably, mouldable. This challenge was met by designing adhesive compositions with exactly the right balance between gel strength and absorption. The inventors hypothesized that such a balance would lead to a more durable product that would be less prone to fall apart during removal or leave residue on the skin.

Clinical Study

In order to test the inventor's hypothesis and follow up on the laboratory tests described above, a clinical study was carried out to confirm the link between the right balance between gel strength and absorption and possible beneficial properties in actual use. In order to build on the laboratory data, the clinical study product was designed to have properties in the relevant intervals, namely a gel strength of 0.9-1.2, an absorption at 2 h of 0.19-0.29 $g/cm^2/2$ h, and an absorption at 24 h of 0.67-1.04 $g/cm^2/24$ h. The composition was provided as a mouldable sealing ring (referred to herein as the "Brava® Protective Seal" or "new seal"). The product was presented to ostomy users and the individual users were asked to compare the new composition to their currently used product. A total of 135 users were included with 34% normally using the Eakin Cohesive, 31% using the Brava Mouldable Ring, 18% using the Adapt product, and 17% using other commercial products.

Results

As an overall result, 53% of the participants indicated a preference for the new seal as compared to their usual seal (see table below).

| Preferred seal | Users |
| --- | --- |
| New seal | 53% |
| Usual seal | 27% |
| No preference | 20% |

This is a very significant result, especially because it is well-known that ostomy users typically are very reluctant to change their products and accessories. Once a user has learned to use a given product and feels comfortable using it, that user is very unlikely to wish to change to a different product. That 53% of the users in the clinical study immediately preferred the new seal over their own current seal is therefore a highly promising result that speaks to the very meaningful advantages experienced by users trying the new seal.

Users evaluated both usual seal and the new seal, Brava® Protective Seal to be easy or very easy to stretch and mold, answered by 81% and 85%, respectively. Easiness of application was also evaluated well; with 75% and 86% answering, that the seal was easy or very easy to apply, for usual and new seal, respectively. In addition, 93% answered that the new seal came off the stomach in one piece, which in comparison was answered by 87% for usual seal.

Sixteen percent of users evaluated high or very high degrees of residues on fingers after application of usual seal versus only 8% after application of new seal. In regards to peristomal skin residues, 23% of users evaluated that the new seal left 'no' residues on the stomach, compared with 6% after test of usual seal. Moreover, 57% reported very few and few residues on the stomach after test of new seal compared with 42% for usual seal. Thus, the new seal left significantly fewer residues on the stomach than usual seal. If there were residues left, the cleaning of skin was also evaluated to be easier after removal of new seal than with usual seal. Also, ostomy bag change is generally made easier and quicker by less residue being left on the skin.

Sixty-nine percent of the users evaluated the new seal to be much or very much durable versus 59% for usual seal. Thus, the new seal was by users evaluated to be significantly more durable than usual.

In line with a high durability, expectations to wear time tend to be evaluated higher for the new seal than for the usual seal.

In supplemental analysis, durability and wear time were explored across type of stoma and brand of seal. Stoma type and usual brand did have some influence on the given evaluations. For all three stoma-types; ileo-, uro- and colostomy users evaluated durability higher (in the best category "very much") for the new seal compared with their usual seal. Users with either an urostomy or a colostomy evaluated durability and expectations to wear time well. For users with an ileostomy the evaluations were two-sided. One out of ten evaluated much higher durability and expectations to wear time than for usual seal and a similar amount evaluated poorer durability and expectations.

After having evaluated usual and new seal, users were asked to give a preference of seal and why. Users should provide a maximum of three reasons. As mentioned herein above, significantly higher preference was observed for the new Brava® Protective Seal compared with the usual seal, with 53% of users preferring the new seal versus 27% who preferred usual seal. The primary reasons for preference of new seal were; due to less residues, evaluated by 56%, and less worry about leakage and better feeling of security, evaluated by 46% of users, on both parameters. The 27% who preferred usual seal, reported it was due to better feeling of security (63%), and less worry about leakage (54%). Preference for usual seal due to less residues was evaluated by only 11%, compared to 56% for the new seal.

Based on the above-described absorption and gel strength tests, durability of the new seal was expected to be better. This was confirmed by the clinical study. The fact that the new seal could easily be removed in one piece, leaving no, few, or very few residues, also support a high durability with low erosion and dissolving during wear.

An interesting observation is the very good evaluation on durability by both users with colostomy and urostomy. A urostomy produces a large amount of fluidly out-put (urine) which potentially may erode the adhesive more easily. Adding to this, many users with an ileostomy, which also produces high amounts of liquid output containing enzymes, also evaluated a high durability of the seal.

In conclusion, users preferred the new Brava® Protective Seal over their usual seal. The new seal was preferred, particularly, because it left fewer residues on fingers and on stomach. Further, it was evaluated to be very durable, and more so compared to usual seal. In relation to easiness of appliance change, users also evaluated the seal to be easy to handle, apply, and remove, and easy to clean away from the peristomal skin.

The clinical study thus confirmed the hypothesized link between striking a balance between gel strength and absorption and achieving beneficial properties, durability in particular, in an actual use situation.

The invention claimed is:

1. An adhesive composition for attachment to skin, the composition comprising 10-14% (w/w) of a polyethylene copolymer, 15-20% (w/w) of a polypropylene glycol, 13-18% (w/w) of a polyolefin, 10-15% (w/w) of a polybutene, 1-5% (w/w) of a wax, 4-8% (w/w) of a polyacrylic acid, and a total of 30-35% (w/w) of one or more absorbent material(s).

2. The adhesive composition according to claim 1, wherein the composition consists of 10-14% (w/w) of the polyethylene copolymer, 15-20% (w/w) of the polypropylene glycol, 13-18% (w/w) of the polyolefin, 10-15% (w/w) of the polybutene, 1-5% (w/w) of the wax, 4-8% (w/w) PAA, and a total of 30-35% (w/w) of one or more further absorbent material(s).

3. The adhesive composition according to claim 1, wherein the composition has an absorption at 2 hours of at least 0.1 g/cm$^2$/2 h per a 6.25 cm$^2$ sample having a 1 mm thickness.

4. The adhesive composition according to claim 2, wherein the composition has an absorption at 24 hours of at least 0.5 g/cm$^2$/24 h.

5. The adhesive composition according to claim 1, wherein the composition has a gel strength where a 1 mm thick sample, soaked in an isotonic saline solution for 24 hours, has a value of below 4 N.

6. An adhesive device for attachment to a skin surface of a user, the device comprising an adhesive composition according to claim 1 and at least one release liner.

7. The adhesive device according to claim 6, wherein the device has a skin-facing surface and a surface facing away from the skin during use, and wherein the release liner is disposed on the skin-facing surface.

8. The adhesive device according to claim 7, wherein a second release liner is disposed on the surface facing away from the skin during use.

9. The adhesive device according to claim 6, wherein the adhesive device is ring or oval shaped with a through-going hole for fitting around a stoma of the user.

10. The adhesive device according to claim 9, wherein the outer diameter of the device is in the range of 30 to 60 mm.

11. The adhesive device according to claim 9, wherein the diameter of the hole is in the range of 10 to 25 mm.

12. The adhesive device according to claim 6, wherein the thickness of the device, including release liner(s) is in the range of 3.5 to 5.5 mm.

13. A method to attach an adhesive device to a patient in need thereof, comprising the steps of
providing an adhesive device according to claim 6;
removing one or more release liners from the adhesive device; and
attaching the adhesive device to a skin surface surrounding a stoma of the patient in need thereof.

14. The method according to claim 13, comprising a further step of attaching the adhesive device to an adhesive baseplate of an ostomy device.

* * * * *

UNITED STATES PATENT AND TRADEMARK OFFICE
CERTIFICATE OF CORRECTION

PATENT NO. : 10,744,224 B2
APPLICATION NO. : 15/754592
DATED : August 18, 2020
INVENTOR(S) : Israelson et al.

It is certified that error appears in the above-identified patent and that said Letters Patent is hereby corrected as shown below:

On the Title Page

Item (74), under "Attorney, Agent, or Firm", in Column 2, Line 2, delete "Nick Bauman" and insert -- Nick Baumann --, therefor.

In the Specification

In Column 7, Line 12, delete "(M(2 hours)" and insert -- (M(2 hours)) --, therefor.

In the Claims

In Column 12, Line 24, in Claim 13, delete "of" and insert -- of: --, therefor.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*